United States Patent [19]

Kudzma et al.

[11] Patent Number: 4,849,521

[45] Date of Patent: Jul. 18, 1989

[54] STEREOSELECTIVE PREPARATION OF 3-SUBSTITUTED-4-PIPERIDINE COMPOUNDS AND DERIVATIVES

[75] Inventors: Linas V. Kudzma, North Bergen; H. Kenneth Spencer, Chatham; Sherry A. Severnak, Plainfield, all of N.J.

[73] Assignee: BOC, Inc., New Providence, N.J.

[21] Appl. No.: 115,276

[22] Filed: Nov. 2, 1987

[51] Int. Cl.$^4$ .......................................... C07D 417/06
[52] U.S. Cl. .................................. 546/209; 546/194; 546/210; 546/211; 546/213; 546/223
[58] Field of Search ............... 546/193, 194, 209, 210, 546/223, 244, 211, 213

[56] References Cited

U.S. PATENT DOCUMENTS

| | | | |
|---|---|---|---|
| 3,161,637 | 12/1964 | Janssen et al. | 546/213 |
| 3,164,600 | 1/1965 | Janssen et al. | 546/213 |
| 3,907,811 | 9/1975 | Janssen et al. | 260/293.77 |
| 3,907,813 | 9/1975 | Janssen et al. | 260/293.79 |
| 3,998,834 | 12/1976 | Janssen et al. | 546/213 |
| 4,196,210 | 4/1980 | Sanczuk et al. | 546/213 |
| 4,584,303 | 4/1986 | Huang et al. | 546/210 |

FOREIGN PATENT DOCUMENTS 0119558 9/1984 European Pat. Off. ............... 211/44

OTHER PUBLICATIONS

D. B. Collum et al., "Substituent Effects on the Stereochemistry, etc", 2/13/84, 4 pgs., J. Am. Chem. Soc. 106, (4865–4869).

T. R. Burke et al., "Probes for Narcotic Receptor Mediated Phenomena, etc.", J. Med. Chem., 1986, 29, 1087–1093, (7 pgs.).

"Drugs for the Future", vol. 9, No. 4, 1984, pp. 197–198 and 262–263.

Primary Examiner—Richard A. Schwartz
Assistant Examiner—Zinna Northington
Attorney, Agent, or Firm—R. Hain Swope; Chris P. Konkol; Larry R. Cassett

[57] ABSTRACT

The present invention is directed to an improved stereoselective tandem substitution and reduction of an imine precursor to the cis form of 3-substituted-4-(phenylanilo)piperidine compounds or their substituted derivatives.

17 Claims, No Drawings

STEREOSELECTIVE PREPARATION OF 3-SUBSTITUTED-4-PIPERIDINE COMPOUNDS AND DERIVATIVES

BACKGROUND OF THE INVENTION

The present invention relates to a stereoselective tandem substitution and reduction reaction of 4-(cinalino) piperidine derivatives. The resulting 3,4-cis compounds are useful intermediates leading to intravenous analgesics.

U.S. Pat. No. 4,584,303 discloses a method of preparing compounds of the following formula:

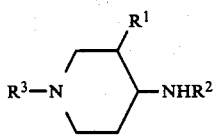

(I)

wherein $R^1$ is a lower alkyl, lower cyclic alkyl, lower alkyl lower cyclic alkyl, lower alkenyl, lower alkyl phenyl; $R^2$ is phenyl or aromatic heterocycle ring either of which may be substituted; and $R^3$ may be a variety of groups including alkyl phenyl. With respect to the $R^1$ and $NHR^2$ substitutents, it is desirable to obtain the more pharmacologically active cis isomer.

The method taught in U.S. Pat. No. 3,584,303 for preparing compounds of formula (I) requires a multi-step synthetic route involving the preparation of cis isomers at an advanced stage of the synthetic route. Furthermore, a cis:trans ratio of not greater than 70:30 can be achieved.

J. Burke, Jr. et al., J. Med. Chem., Vol. 29, No. 6, pp 1087–1093 (1986), discloses a method to prepare piperidine derivatives, which method suffers the same disadvantages of the above-mentioned prior art method. Furthermore, the multi-step method of Burke et al. requires expensive starting materials and protection of the piperidine nitrogen.

The deprotonation of aliphatic imines followed by alkylation is generally known as, for example, shown by Collum et al., J. Am. Chem. Soc., Vol. 106, pp 4865–4869 (1984). The reduction of an imine is in itself also conventional.

SUMMARY OF THE INVENTION

The invention is directed to a method of preparing a compound of the following formula:

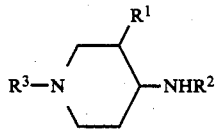

wherein $R^1$ is lower alkyl, lower cylic alkyl, lower alkyl lower cyclic alkyl, lower alkenyl, or lower alkyl phenyl; $R^2$ is a phenyl or aromatic heterocycle ring either of which may be substituted with one or more groups selected from the group consisting of lower alkoxy, lower alkyl, halogen, or combinations thereof; and $R^3$ can be a wide variety of groups, for example, selected from phenyl lower alkyl, thiazolyl lower alkyl, which can be substituted in the 4-position with a lower alkyl group, (4,5-dihydro-5-oxo-1H-tetrazol-1-yl) lower alkyl, which can be substituted in the 4-position with a lower alkyl, and substituted phenyl lower alkyl in which the substituents on the phenyl ring are selected from halogen, lower alkoxy, lower alkyl or combinations thereof.

According to the method of the present invention, an aryl imine precursor is capable of being stereoselectively substituted in a single reactor without requiring intermediate separations or purifications. Readily available starting materials are utilized and no special protection of the piperidine nitrogen is necessary. Very high selectivity of the cis isomer (typically 96%) can be achieved, resulting in an easier purification at an early stage of the overall synthetic route leading to the final product. Production of the nonrecyclable trans isomer is minimized.

DETAILED DESCRIPTION OF THE INVENTION

Applicants have found an improved method for the efficient and economical preparation of compounds according to formula (I) below:

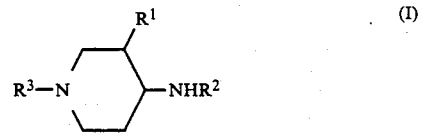

(I)

wherein $R^1$ is lower alkyl, lower cyclic alkyl, lower alkyl lower cyclic alkyl, lower alkenyl, or lower alkyl phenyl; $R^2$ is a phenyl or aromatic heterocycle ring either of which may be substituted with one or more groups selected from the group consisting of lower alkoxy, lower alkyl, halogen, or combinations thereof; and $R^3$ is selected from a wide variety of groups, including phenyl lower alkyl, thiazolyl lower alkyl, which can be substituted in the 4-position with a lower alkyl group, (4,5-dihydro-5-oxo-1H-tetrazol-1-yl) lower alkyl, which can be substituted in the 4-position with a lower alkyl, and substituted phenyl lower alkyl in which the substituents on the phenyl ring are selected from halogen, lower alkoxy, lower alkyl or combinations thereof.

By the term lower alkyl, lower alkoxy, lower cyclic alkyl, or lower alkenyl are meant branched or unbranched chain groups with seven or less carbon atoms and preferably 5 or less carbons. By aromatic heterocycle ring is meant a fully unsaturated ring having 5 or 6 members including 0–3 nitrogen atoms and 0–2 oxygen or sulfur atoms. The term halogen is meant to include fluoro, chloro, bromo, or iodo substituents.

Examples of suitable $R^1$ groups include methyl, ethyl, cyclopropyl, cyclopropylmethyl, allyl and benzyl.

Examples of suitable $R^2$ groups include phenyl, 2-fluorophenyl, 2-methylphenyl, 2-methoxyphenyl, pyrazolyl, or thienyl.

Examples of suitable $R^3$ groups include phenyl ethyl, 2-(4-ethyl-4-4,5-dihydro-5-oxo-1H-tetrazol-1-yl)ethyl, and 2-(4-methyl-thiazoyl)ethyl.

The route to compounds of the formula (I) proceeds as follows:

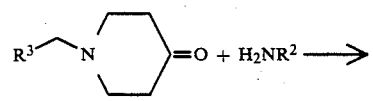

-continued

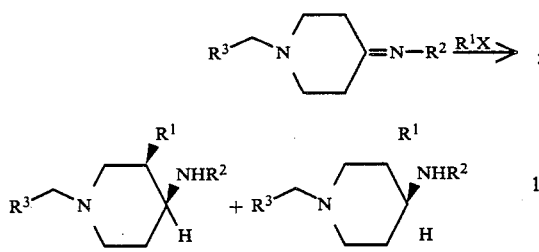

wherein R¹, R² and R³ are as defined above and R¹X is a reagent capable of adding the R¹ group to the 3 position of the piperidine ring, for example, a lower alkyl iodide alkylating agent.

It is noted that the present invention does not involve the N-substituted-3-substituted-4-piperidone intermediate compound conventionally employed, for example, in the prior art synthetic route of U.S. Pat. No. 4,584,303. This latter compound is difficult to make. Instead, Applicants' above described reaction scheme begins with the intermediate compound N-substituted-4-piperidone, which is commercially available from Aldrich Chemical Co. (Milwaukee, Wisc.) or Chemical Dynamics Corp. (So. Plainfield, N.J.) or else easily made by a Mannich condensation, as will be readily appreciated by those skilled in the art. The latter piperidone compound is then reacted with a substituted or unsubstituted phenyl amine or aromatic heterocyclic amine to form the imine precursor (III) above. This reaction is suitably carried out in the presence of p-toluene sulfonic acid and refluxed while collecting water. The imine precursor (III) is then stirred at a low temperature with a non-nucleophilic base such as freshly prepared lithium diisopropyl amide in order to deprotonate the imine. Other suitable non-nucleophilic bases include LDC (lithium dicyclohexylamide), LIC (lithium isopropylcyclohexylamide), LTP (tetramethylpiperamide) and LHS [lithium bis(trimethylsilyl)]amide.

By removal of the alpha (to the schiff base) proton, the following anion is generated:

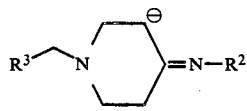

(IIIa)

Addition of a substituting agent R¹X such as the alkylating agent alkyl iodide results in the anion IIIa attaching the electrophile R¹X to form the following alkylated imine intermediate.

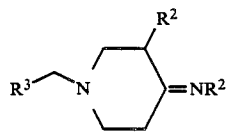

(IIIb)

The most preferred substituting agents are iodides, bromides and chlorides. Tosylates and mesylates and other substituting agents known to those skilled in the art are also suitable.

Finally, without the necessity of isolating (IIIb), a very selective reduction to the desired valuable intermediate (IV) above is carried out. This reduction is a steric approach control reaction wherein the least crowded side of the intermediate (IIIb) is preferably attached by a relatively highly hindered reducing agent such as the hindered borohydride reducing agents.

The most preferred reducing agent is "Super-Hydride" because of its superior combination of cis selectivity and speed. Other preferred hindered borohydride reducing agents include L-selectride (lithium tri-sec-butylborohydride, 1.0 molar in THF) and Nβ-Enantride (lithium hydride, a 9-ββN-nopolbenzyl ether adduct, 0.5 molar in THF). A cis:trans selectivity of greater than 90 percent and typically 96 percent is thereby obtainable. Other suitable reducing agents include Red-Al (sodium bis(2-methoxy-ethoxy)aluminum hydride, 3.4 molar in toluene, and LiAlH₄. Typically, a selectivity of only about 60–70 percent cis:trans is obtained with the latter reducing agents. All of the above named reducing agents are commercially available from Aldrich Chemical Co. (Milwaukee, Wisc.).

A major advantage of the above described synthetic route is that the reactions occur in a single vessel by the sequential introduction of the necessary reactants. Consequently, successive isolations and purifications are obviated, thereby greatly simplifying the overall route to a variety of therapeutic agents, notably of the fentanyl type, which are used in humans for inducing anesthesia or analgesia, for example A-3331. The remaining steps in the overall synthesis to such compounds are disclosed in detail in U.S. Pat. No. 4,584,303 to Huang et al., which hereby is incorporated by reference. Other compounds which may be prepared by a synthetic route within the scope of the present invention include β-hydroxyl-3-methylfentanyl and cis-3-methyl fantanyl (known in the chemical and pharmaceutical literature as F-7302 and R 26,800, respectively) which have demonstrated potent analgesic activity.

EXAMPLE 1

This example illustrates the preparation of 1-benzyl-3-(cis-methyl)-4-[N-(20fluorophenyl)amino]piperidine.

A solution of 1-benzyl-4-piperidone, 15.20 gms (80.31 mmol), 2-fluoroaniline, 9.02 gms (81.17 mmol) and p-toluenesulfonic acid monohydrate, 0.48 gms in 200 ml of toluene was refluxed overnight under argon collecting water in a Dean-Stark trap. After 18 hours the theoretical amount of water had separated and the trap was drained several times to distill off 100 mls of toluene. The reaction was cooled under argon and diluted with 40 mls anhydrous THF. The deep orange solution of crude imine 1 was used "as is" for next step.

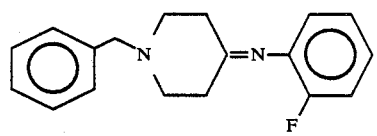

LDA was prepared under an atmosphere of argon by adding freshly distilled diisopropyl amine, 15 ml (107 mmol) dropwise to a cold (0° C.) solution of 55 mls of 1.6M n-butyllithium (88 mmol) in hexane in 60 mls of anhydrous THF. After 15 minutes at 0° C. the LDA solution was cooled to −78° C. in an isopropanol-dry ice slush bath. The solution of imine 1 (80.31 mmol) was added dropwise with stirring. The reaction was stirred at −78° C. for 1 hour followed by rapid addition of methyl iodide, 12.9 gms (90.88 mmol). The reaction was stirred at −78° C. for 15 minutes followed by warming to room temperature. After 10 minutes at −78° C. a precipitate formed which redissolved as the reaction warmed up. After stirring at room temperature for 2 hours the reaction was cooled to 0° C. in an ice bath and 120 mls 1.0M Lithium triethlyborohydride in THF was added dropwise via syringe. The reaction was stirred overnight (16 hours) warming to room temperature. The reaction was then cooled back down to 0° C. and 50 mls of water was added slowly dropwise (exotherm and vigorous gas evolution). The quenched reaction mixture was concentrated to a pasty oil which was dissolved in 200 mls toluene and washed with 100 mls of water. The toluene layer was separated, dried over anhydrous sodium sulfate and concentrated to give a crude mixture of cis and trans diamine. Analytical LC showed the cis/trans diamine ratio to be 92.2:7.8. This crude oil was flash chromatographed on Silica 60, 230-400 mesh (400 gms) eluting with 1:10 EtOAc/Hex with 0.1% ammonium hydroxide added to give 9.74 gms pure cis diamine (40.6%) shown below and 1.57 gms cis and trans diammine mixture. Total isolated yield of cis and trans diammine was 47.2%.

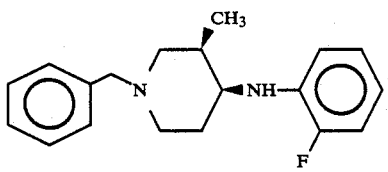

M.P.: 55°–56° C.

NMR: 7.40(s,5H), 7.20–6.35(m,4H), 3.90(br s,1H), 3.40 (br s,2H), 3.00–1.30(complex,8H), 0.95(d,3H)

EXAMPLE 2

In an analogous manner to the synthesis of Example 1, except using allyl bromide as the substituting agent, the compound 1-benzyl-3-(cis-allyl)-4-[N-(2-fluorophenyl)amino]piperidine was prepared having the following formula:

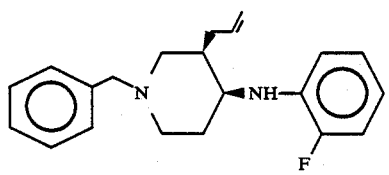

oil at room temperature

NMR: 7.30 (m,5H), 6.95(m,2H), 6.60(m,2H), 5.65(m,1H), 4.45(m,2H), 3.95(br 2,1H), 3.60(m,1H), 3.50 (ABq,2H), 2.60–1.65(complex,9H)

EXAMPLES 3-5

In an analogous manner to the synthesis of Example 1, except using 1-iodopropane, benzyl bromide, and (bromomethyl)-cyclopropane, respectively as the substituting agent, the following compounds were prepared:

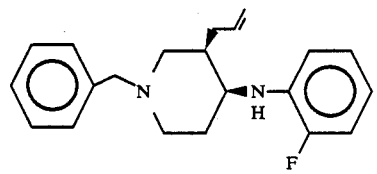

1-benzyl-3-[cis-(n-propyl)]-4-[N-(2-fluorophenyl)amino]-N piperidine oil at R.T.

NMR: 7.40(s,5H), 7.40–6.50(m,4H), 3.95(br s, 1H), 3.60(m,1H), 3.50(ABq,2H), 2.60–0.30(complex,14H)

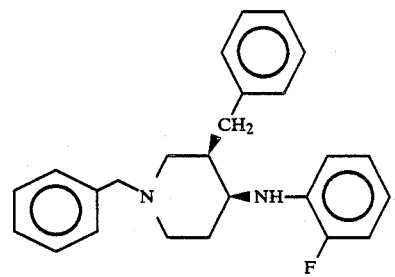

1-benzyl-3-(cis-benzyl)-4-[N-(2-fluorophenylamino)]-piperidine oil at R.T.

NMR: 7.40–6.40(complex,14H), 4.05(m,1H), 3.50(br s,2H). 3.85–1.45(complex,10H).

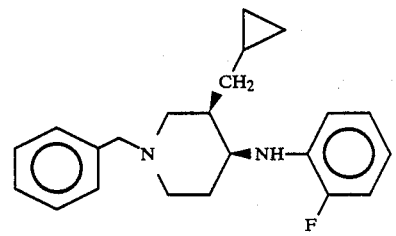

1-benzyl-3-[cis-(cyclopropyl)methyl]-4-[N-(20fluorophenylamino)]piperidine oil at R.T.

NMR: 7.50–6.50(m,9H), 4.35(m,1H), 3.40(br s,2H) 3.35–0.80(complex,10H), 0.60–0.05(m,5H)

It will be understood that the embodiments described herein are merely exemplary and that a person skilled in the art may make variations and modifications without departing from the spirit and scope of the invention. All such modifications and variations are intended to be included within the scope of the invention as defined in the appended claims.

We claim:

1. A method of preparing the cis isomer of a 4-anilino-3-$R^1$-piperidine, wherein $R^1$ is lower alkyl, lower cyclic alkyl, lower alkyl lower cyclic alkyl, lower alkyl phenyl, or lower alkenyl, said method comprising:
   (i) depronating a 4-imine piperidine with a non-nucleophilic base to form a deprotonated anion at the 3-position of the piperidine ring;
   (ii) reacting said deprotonated anion with a substituting agent to introduce an $R^1$ group in said 3-position; and
   (iii) reducing the compound resulting from step (ii) to produce the cis isomer thereof, whereby a cis:trans selectivity of greater than about 90 percent is obtainable.

2. A method of preparing a compound of the formula:

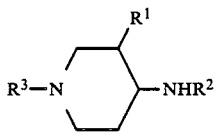 (1)

wherein $R^1$ is a lower alkyl, lower cylic alkyl, lower alkyl lower cyclic alkyl, lower alkenyl or lower alkyl phenyl; $R^2$ is a phenyl which may be substituted with one or more substituents selected from the group consisting of lower alkoxy, lower alkyl, halogen or combinations thereof, and $R^3$ is selected from the group consisting of phenyl-lower-alkyl, thiazoyl lower alkyl which can be substituted in the 4-position with a lower alkyl group, (4,5-dihydro-4-oxo-1H-tetrazol-1-yl) lower alkyl which can be substituted in the 4-position with a lower alkyl, and substituted phenyl lower alkyl in which the substitutents on the phenyl ring are selected from halogen, lower alkoxy, lower alkyl, or combinations thereof; said method comprising:

(i) deprotonating a compound of the following formula:

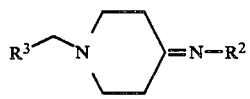

with a non-nucleophilic base to form a deprotonated anion at the 3-position of the piperidine ring;

(ii) reacting said anion with a substituting agent to introduce said Rgroup in said 3-position; and (iii) reducing the compound resulting from step (ii) to produce the compound (1) above, thereby obtaining the cis isomer thereof, whereby a cis:trans selectivity of greater than about 90 percent is obtainable.

3. The method of claim 1 or 2, wherein said non-nucleophilic base is a lithium lower alkyl amide.

4. The method of claim 3, wherein said lithium lower alkyl amide is selected from the group consisting of lithium diisopropylamide, lithium dicyclohexylamide, lithium isopropylcyclohexylamide, lithium tetramethylpiperamide and lithium bis (trimethylsilyl)amide.

5. The method of claim 1 or 2 wherein said substituting agent is an alkylating agent.

6. The method of claim 1 or 2 wherein said deprotonating is carried out in a solvent comprising tetrahydrofuran.

7. The method of claim 5, wherein said alkylating agent is an iodide or tosylate.

8. The method of claim 7, wherein said iodide is an alkyl iodide.

9. The method of claim 1 or 2, wherein said reducing is by means of a hindered borohydride reducing agent.

10. The method of claim 9, wherein said hindered borohydride reducing agent is selected from the group consisting of lithium triethylborohydride, lithium tri-sec-butylborohydride, or lithium hydride 9-$\beta\beta$N-nopolbenzylether adduct.

11. The method of claim 1 or 2, wherein said steps (i) through (iii) are carried out continuously without purification or isolation of intermediates.

12. The method of claim 11, wherein the said steps (i) through (iii) are continuously carried out in the same reactor means.

13. The method of claim 1 or 2, wherein said cis isomer is purified from minor amounts of the trans isomer.

14. A method of preparing a compound of the formula:

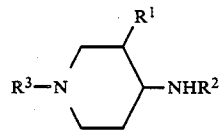

wherein $R^1$ is a lower alkyl, lower cylic alkyl, lower alkyl lower cylic alkyl, lower alkyl, lower alkenyl, or lower alkyl phenyl; $R^2$ is a phenyl, which may be substituted with one or more substituents selected from the group consisting of lower alkoxy, lower alkyl, halogen or combinations thereof, and $R^3$ is selected from the group consisting of phenyl-lower-alkyl, thiazoyl lower alkyl which can be substituted in the 4-position with a lower alkyl group, (4,5-dihydro-4-oxo-1H-tetrazol-1-yl) lower alkyl which can be substituted in the 4-position with a lower alkyl, and substituted phenyl lower alkyl in which the substituents on the phenyl ring are selected from halogen, lower alkoxy, lower alkyl, halogen or combinations thereof; said method comprising:

(i) reacting $H_2NR^2$ with a compound of the following formula:

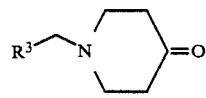 (2)

(ii) deprotonating the compound of formula (2) with a non-nucleophilic base to form a deprotonated anion at the 3-position of the piperidine ring;

(iii) reacting said anion with a substituting agent to introduce an $R^1$ group in said 3-position; and (iv) reducing the compound of step (ii) to produce the compound (1) above, thereby obtaining the cis isomer thereof, whereby a cis:trans selectivity of greater than about 90 percent is obtainable.

15. The method of claim 14, wherein said substituting agent is an alkylating agent.

16. The method of claim 15, wherein said non-nucleophilic base is a lithium lower alkyl amide.

17. The method of claim 14 wherein said compound is reduced by introducing a hindered borohydride reducing agent.

* * * * *